United States Patent [19]

Liedtke

[11] Patent Number: 4,765,986
[45] Date of Patent: Aug. 23, 1988

[54] MEDICINAL PLASTER FOR SYSTEMIC USE

[76] Inventor: Rainer K. Liedtke, Tölzer Str. 36, 8022 Grünwald, Fed. Rep. of Germany

[21] Appl. No.: 875,100

[22] Filed: Jun. 17, 1986

[30] Foreign Application Priority Data

Jun. 20, 1985 [DE] Fed. Rep. of Germany ....... 3522060

[51] Int. Cl.⁴ .............................................. A61F 13/00
[52] U.S. Cl. ..................................... 424/449; 424/448
[58] Field of Search ................................ 424/449, 448

[56] References Cited

U.S. PATENT DOCUMENTS

| 4,552,751 | 11/1985 | Inaba et al. | 424/449 |
| 4,568,343 | 2/1986 | Leeper et al. | 424/449 |
| 4,573,995 | 3/1986 | Chen et al. | 424/449 |
| 4,681,582 | 7/1987 | Yamamoto | 424/486 X |

Primary Examiner—Thurman K. Page
Assistant Examiner—L. R. Horne
Attorney, Agent, or Firm—Oblon, Fisher, Spivak, McClelland & Maier

[57] ABSTRACT

A medicinal plaster for dermally applied medication which is attachable to the skin, which comprises first and second parts joined in a housing which is closed at the top side and open on the lower side thereof towards the skin surface, said first part at the lower side comprising a drug-containing carrier substance which melts at approximately physiological body temperature; and said second part at the top side, which is affixed to said first part, comprises a porous and flexible synthetic material having approximately the same diameter as said first part.

9 Claims, 2 Drawing Sheets

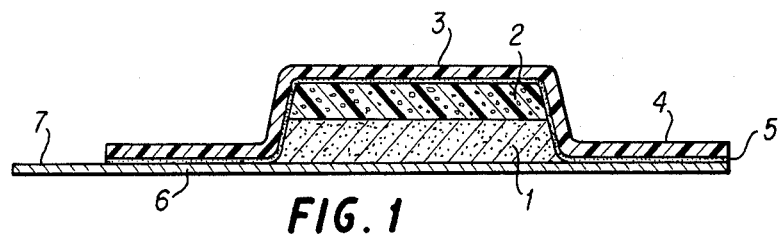
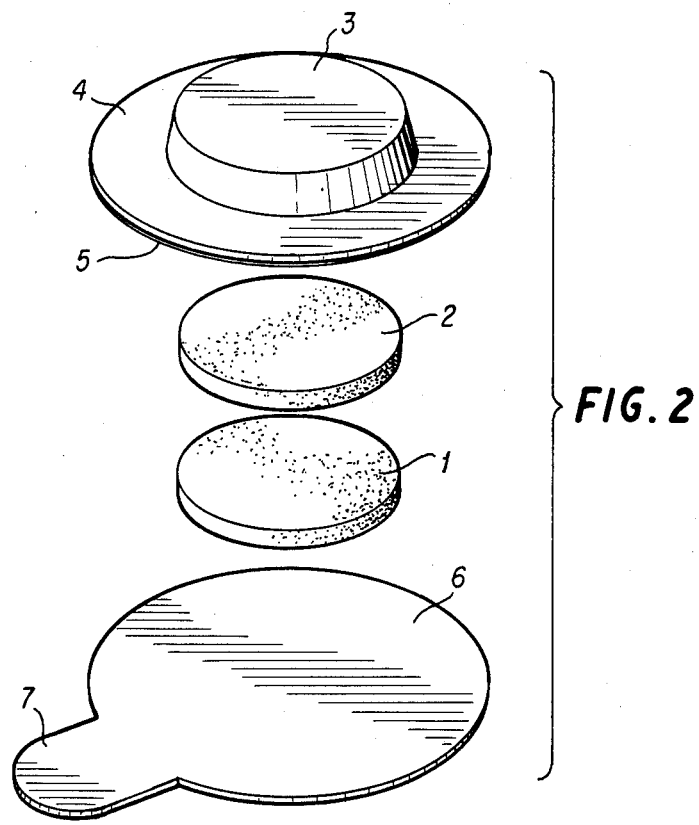
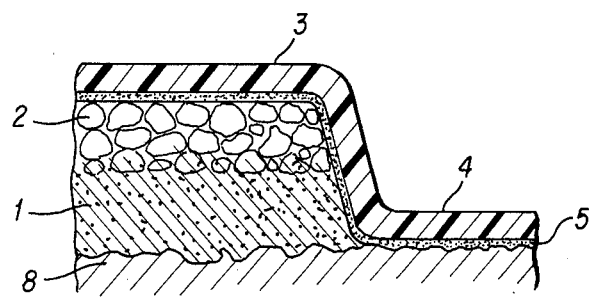

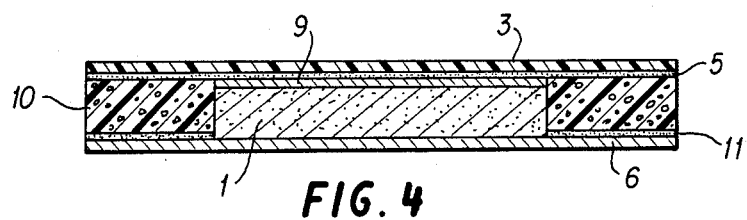
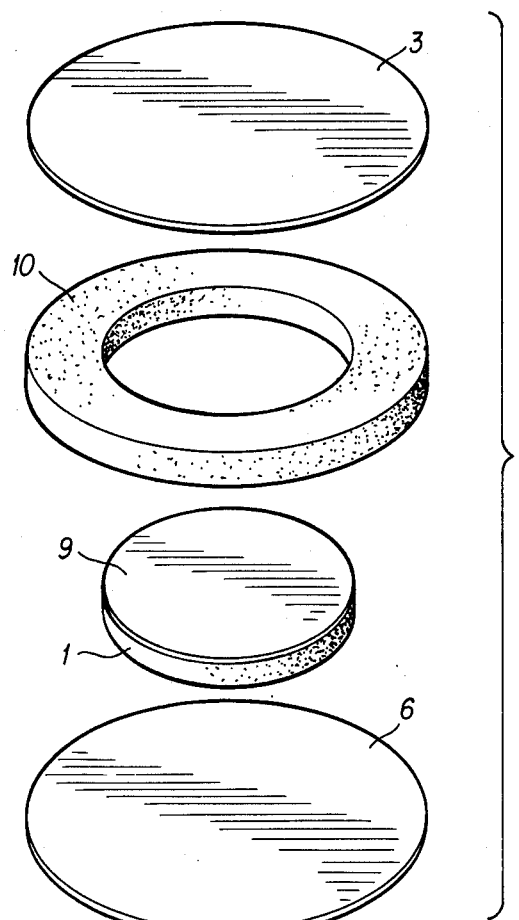

MEDICINAL PLASTER FOR SYSTEMIC USE

BACKGROUND OF THE INVENTION

1. Field of the Invention

The present invention relates to a medicinal plaster for improved skin absorption of dermally applied medication.

2. Description of the Background

It is known that systemic medicinal effects can be obtained with medicinal plasters or so-called therapeutic plaster systems, designated lately as transdermal therapeutic systems. At present, this type of system is used in connection with the drug scopolamine for kinetosis, nitroglycerine for coronary heart disease and clonidine for hypertension, as well as for transdermally administered estrogens. However, the plaster systems used to date are technically complex and the attainable absorption rates, measured through the systemic drug concentration in the blood, are clearly less than those after oral administration. In addition, the systems show considerable variation from patient to patient with regard to the determined serum concentrations of the administered drugs.

The plaster systems entail diffusion units in which the medications are released by diffusion at controlled rates from a mechanically fixed drug reservoir, usually tissue tolerant polymers. The systems used are currently divided into membrane systems, i.e., membrane plaster and matrix systems. In the membrane systems the drug, after release from the carrier substance, must permeate a membrane, which serves as a control element for the constant absorption rate. Thereby, it is possible to attain a release characteristic, which approximately corresponds to pharmacokinetics of zero order. In matrix systems, the drug stored in depot form diffuses directly from the polymer matrix into the skin.

The transfer of medication from the plaster system into the skin occurs according to the laws of diffusion, quantified in the diffusion principles according to Fick:

$$\frac{dQ}{dt} = D \cdot F \frac{c_1 - c_2}{d}$$

whereby per time unit (t) the drug amount transported (Q), the diffusion rate, is dependent on the diffusion coefficient (D), the exchange surface (F) and the concentration difference ($c_1-c_2$) as well as the diffusion distance or the layer thickness (d). It is observed that plasters with mechanically rigid matrices do not optimally follow the diffusion conditions.

Thus, the polymer matrices and biological membranes such as irregularly formed complementary skin surface, which represent the exchange surface, adhere such that there is an incomplete utilization of the biologically available absorption surface. Simultaneously, the diffusion distance is thereby increased in several areas of the adhering absorption surface of the plaster. Both effects mean a deterioration of the general diffusion conditions. As, in addition, the speed of the diffusion process also depends on the temperature, the temperature exchange between the technical resorption area and the drug reservoir on the one hand, and the skin surface on the other hand, is not optimally attained with the incomplete superposition. Another disadvantageous effect is the relatively slow water absorption which is needed for the dissolving process of the medication.

In addition, the production of membrane and matrix systems is technically costly and requires special apparatus, which causes higher costs than for the production of oral forms of application.

Accordingly, a need clearly exists for a relatively simple and inexpensive means by which dermally applied medications can be applied with excellent skin absorption.

SUMMARY OF THE INVENTION

Accordingly, it is an object of the present invention to provide a relatively simple and inexpensive means by which dermally applied medications can be administered with excellent skin absorption.

According to the present invention, the foregoing and other objects are attained by providing a medicinal plaster for dermally applied medication which is attachable to the skin, which entails two joined parts in a housing which is closed at the top and open on the lower side towards the skin surface, said first part at the lower side being a drug-containing carrier substance which melts at physiological body temperature; and said second part at the top side, being affixed to said lower side carrier substance, is a porous and flexible synthetic material having approximately the same diameter as said lower side disk.

BRIEF DESCRIPTION OF THE DRAWINGS

FIG. 1 illustrates the present medicinal plaster in a cross-sectional view.

FIG. 2 illustrates the present medicinal plaster in an exploded diagram.

FIG. 3 illustrates a partial enlargement of the present medicinal plaster in a cross-sectional view.

FIG. 4 illustrates a detailed modification of the present medicinal plaster in a cross-sectional view.

FIG. 5 illustrates a detailed modification of the present medicinal plaster in an exploded diagram.

DETAILED DESCRIPTION OF THE PREFERRED EMBODIMENT

According to the present invention, the medication is contained in a solid carrier substance, preferably shaped as a disk, which melts at physiological body temperature, whereby the carrier substance is affixed to the bottom side of a porous and flexible synthetic material of approximately the same diameter and the two joined parts are located in a housing, closed on top and open towards the skin side, which may be attached to the skin.

In a further aspect of the present invention, it is possible to utilize non-homogeneously dissolving drugs which are absorbed in the carrier substance in pharmaceutical technical depot form in order to provide for delayed drug release.

In another aspect of the present invention, two or more layers having varying melting behavior are applied on top of each other in order to attain a varying successive absorption rate.

In a further aspect of this invention, the carrier substance is distributed in the pores of the whole synthetic material in order to better retain the full flexibility of the synthetic material.

In another aspect of this invention, the synthetic material is provided on its top side with a mechanical barrier layer in order to obtain a better mechanical separation between carrier substance and housing.

In still a further aspect of this invention, the synthetic material is preferably made of polyurethane foam of the ether type or of the ester type in order to attain particularly favorable physical properties together with a physiological indifference or tolerance.

In another aspect of the present invention, carrier substances of solid fats/adeps solidus or mixtures of various solid fats are preferably introduced into the pores of a synthetic material of polyurethane foam of the ether type or ester type, in order to obtain particularly favorable physical and biopharmaceutical properties together with a good physiological tolerance.

According to the present invention, carrier substances of gelatin or mixtures of gelatin and solid fats are preferably introduced into the pores of a synthetic material or polyurethane foam of the ether type or ester type, in order to obtain particularly favorable physical and biopharmaceutical properties, together with a good physiological tolerance. However, other suitable carrier substances meeting the above requirements may also be used. Additionally, medium chain partial glycerides or mixtures of partial glycerides may be introduced into the carrier substance in order to improve the release of lipophile drugs ard to affect a regulation of the physical and biopharmaceutical properties of the carrier substance. Also, hydrophilic auxiliary materials may be introduced into the carrier substance in order to improve the release of hydrophile drugs from the carrier substance.

In another aspect of this invention, a one-sided self-adhesive plastic foil in connection with a one-sided self-adhesive foam ring with closed pores is used, whereby the carrier substance is joined to the bottom side of the plastic foil and placed in the opening of the foam ring, in order to obtain a better skin adhesion of the drug plaster in connection with a sufficient occlusion effect as well as a better protection of the carrier substance against thermal and mechnical influences.

The many advantages attained with the invention result predominantly from the fact that the drug release from the bottom of the carrier substance is enhanced by the melting process induced by the skin temperature and that the transfer into the skin occurs from the liquid phase of the carrier substance. As the carrier substance spreads as a liquid film, the total available complementary skin surface is covered even in its micro topography, contrary to the mechanically more inflexible systems which adhere flat and thus not fully, and also reach the deeper set integumentary system, such as sebaceous glands and sweat glands which present a considerable absorption area. Because of the direct adherance of the liquid phase of the carrier substance, the need for an additional adhesive foil in the absorption area, as is the case with mechanically fixed systems, is eliminated. The tight contact between the liquid phase of the carrier substance and the skin into the micro topographic area also simultaneously reduces the average diffusion distance. Thus, the optimal surface utilization of the available skin absorption area and the reduction of the diffusion distance also provide advantages in the diffusion conditions as compared to the mechanically fixed systems. The specific transport conditions through the skin surface for the various drugs, which occur according to the laws of the so-called 'non-ionic diffusion' are favored overall.

It should be noted that while the carrier substance and the flexible synthetic material may have any shape, they are preferably disk-shaped.

The effects obtained with the successively melting carrier substance disk are comparable to the external application of liquid or viscous preparations, such as salves and sprays, or the internal use of stomach gels or suppositories. However, contrary to the application of salves and sprays, there is no drying of the carrier substance due to evaporation and thus a reduction of the dissolution conditions. Because of its cover, the plaster system much rather creates a moist chamber, which in turn improves the penetration of the medication by increasing the hydration of the arid stratum corneum.

As it is possible to produce for each drug specific galenically optimal carrier substance disks, depending on its physical chemical properties, the system is—with a constant basic configuration—versatile and technologically simple. Contrary to the dermal application of salves, gels and sprays, the system delivers exact dosages. There is also no danger of contamination or loss of medication by outside influences.

As no mechanical component, such as membranes or adhesive foil, is applied between the carrier substance and the skin, there is also no mechanical irritation by friction from this source. While muscular motions or temporary surface changes in the adhesive area, e.g. due to breathing movements in the thorax area, can—in mechanical systems—interfere with the adhesive quality of the adhesive foil or cause a constant mechanical irritation, this effect is rather advantageous with the carrier substance disk, the bottom surface of which is always present as a liquid phase, as it favors the distribution and thus produces a surface increase into the micro topography of the skin, similar to an application of salve.

As the production of the carrier disk, e.g. by simple moulding or pressing, as in the production of suppositories, is less costly than the production of exactly dosed polymer matrices or membrane systems, it is also possible to reduce production costs using the present invention.

Furthermore, it is also possible to include into the carrier disk, apart from homogeneously distributed drugs, pharmaceutically-technically restrained formulations, which have an independently release characteristic, so that a rapid as well as a delayed absorption component can be simultaneously realized in the system. Another possibility for the control of varying release characteristics is the application of several carrier substance disks with varying melting behavior.

Due to the partial penetration of the carrier substance into the pores of the flexible elements, a firm contact between the two components is assured, so that, even with possible damage to the carrier substance disk in the solid state, it does not separate fully or in part from the flexible element. The flexible element also assures, independent from the position of the plaster application, a constant adhesion and thus a firm contact between the carrier substance disk and the skin surface.

Other effects can be attained through the skin temperature, which controls the speed of the melting process. Thus, with a raised skin temperature, e.g. during a fever condition, the melting process and the thus resulting drug release is speeded up. With falling skin temperature, e.g. caused by the transdermally released drug with antipyretic properties, the release speed is again reduced. Such a process corresponds to a direct biological feedback with opposite control effect on the medication release.

Various aspects of the present invention are illustrated in the figures, whereby the examples illustrate the invention, without restricting the same.

The medication is in the carrier substance (1), produced as flat disk. This, in turn, is attached to the bottom side of a porous and flexible synthetic material disk, whereby parts of the carrier substance penetrate into the pores of the synthetic material disk. The latter effect is particularly shown in the partial enlargement of the cross section in FIG. 3. The carrier substance disk and the synthetic material disk are located in a housing (3), closed on top, serving as cover layer, which has a circular rim (4). The inside of the housing, as well as the bottom side of the rim are provided with an adhesive layer (5). The adhesive layer inside the housing is used for attaching the synthetic material disk, the adhesive layer of the rim is used for attaching the plaster to the skin surface.

The open lower side of the housing with the carrier substance disk is firmly closed off by a removable foil (6) which sticks to the rim. The foil has dimensions which fully cover the total lower surface including adhesive rim. On one side, a part of the foil protrudes beyond the adhesive rim (7). This part provides for an easy pulling off of the foil from the adhesive surface. Shown in FIG. 3 is, apart from the mechanical connection between carrier substance disk and synthetic material disk by the penetration of the carrier substance into the pores of the synthetic material disk, also, schematically, the distribution of the liquid phase of the carrier substance on the irregularly structured micro topography of the skin surface (8).

In the modification of the basic system, as shown in FIGS. 4 and 5, the top side of the housing is level. The top side of the housing consists of an occlusive plastic foil (3), which is provided with an adhesive layer (5) along its bottom side. In the center part of the lower side of the occlusive plastic foil, the upper side of the synthetic material disk (1) is glued on, whereby this upper part of the synthetic material disk is constructed as mechanical barrier (9), which prevents the diffusion of the drugs into the adhesive zone of the occlusive plastic foil. Glued to the outer area of the lower side of the plastic foil is s circular foam ring (1) made of closed pore polymer material, which, in turn, has an adhesive layer (11) on its lower side. This adhesive layer is used for attaching the medicinal plaster to the skin. The synthetic material disk containing the carrier substance (1) is located in the central opening of the foam ring (10). On the lower side of the synthetic material disk, facing the skin surface, there is a mechanically sealed protective foil (6) with the dimension of the total diameter of the plaster, which is circularly connected to the rim of the adhesive layer of the foam ring (11) and can be removed before applying to the skin.

Shown in FIG. 5 is the medicinal plaster in an exploded diagram, which shows the main layers plastic foil (3), foam ring (10), synthetic material disk with carrier substance (1) and removable protective foil (6).

According to the present invention, any drug may be delivered through the present medicinal plaster. However, particularly useful drugs are those which can be absorbed by the skin based upon their physicochemical properties. For example, drugs such as those used in the treatment of high blood pressure or angina pectoris may be used. Such drugs are the so-called calcium antagonists, and β-blockers, which are well-known to those skilled in the art.

The medicinal plaster of the present invention may be used on the surface of any mammalian skin such as a dog or cat but, preferably human skin. The medicinal plaster is attached to the skin and is charged with an effective amount of medication for the intended purpose. Of course, the precise amount of medication used will vary depending upon the mammalian or human body weight, the nature of the drug and the nature of the treatment. However, such amounts would be known to those skilled in the art in view of the above disclosure.

Having now fully described this invention, it will be apparent to one of ordinary skill in the art that many changes and modifications can be made thereto without departing from the spirit or scope of the invention as set forth herein.

The term "adeps solidus" is a synonym for "solid fats".

The term "solid fats" comprises triglycerides of saturated carbon acids having 10 to 18 carbon atoms in the chain.

The term "medium chain length partial glycerides" comprises mono- and diglycerides of saturated and/or unsaturated carbon acids having 8 to 12 carbon atoms in the chain.

The term "gelatin" comprises a hydrolysis product of ossein.

The term "polyurethan foam of the ether/ester type" comprises reaction products of polyfunctional isocyanates with polyesters or polyethers containing hydroxyl groups.

What is claimed is:

1. A medicinal plaster for dermally applied medication which is attachable to the skin, which comprises first and second parts joined in a housing which is closed at the top side and open on the lower side thereof towards the skin surface, wherein said first part at the lower side is a disc comprising a drug-containing carrier substance, said carrier substance being selected form the group consisting of gelatin; one or more triglycerides of unsaturated carbon acids having 10-18 carbon atoms; and a mixture of one or more of said triglycerides of saturated carbon acids having 10-18 carbon atoms and one or more mono- and diglycerides of saturated and unsaturated, or both, carbon acids having 8-12 carbon atoms; and a mixture of gelatin with one or more of said triglycerides; and a mixture of gelatin with a one or more of said triglycerides and one or more of said mono- and diglycerides; said carrier substance melting at approximately physiological body temperature so that the drug is released from the liquid phase of the carrier substance; and said second part is a disc consisting of a porous and flexiable polyurethane-ether foam or polyurethane-ester foam having approximately the same diameter as said first part; said carrier substance disc being mechanically connected with the polyurethane foam disc by at least partial penetration of the carrier substance into the pores of the polyurethane foam disc.

2. The medicinal plaster according to claim 1, wherein said drug contained in said carrier is not exclusively homogeneously dissolved and is contained in said carrier substance in technical depot form.

3. The medicinal plaster according to claim 1, wherein the drug-containing carrier substance is distributed in the pores of the polyruethane foam disc.

4. The medicinal plaster according to claim 1, wherein the polyurethane foam disc has a mechanical barrier at the top side thereof.

5. The medicinal plaster according to claim 1, wherein the plaster is one-sided self-adhesive plastic foil on the lower side of which is a one-sided self-adhesive closed pore foam ring and, in the whole of the foam ring, the polyurethane foam disc with carrier substance is joined to the plastic foil.

6. The medicinal plaster according to claim 1, wherein the carrier contains one or more drugs for the treatment of high blood pressure or angina pectoris in an amount of 0.5–10% by weight based on the carrier substance.

7. The medicinal plaster according to claim 6, wherein said carrier contains 2–8% by weight of said drugs.

8. A method of dermally administering medication with enhanced skin absorption, which comprises attaching the medicinal plaster of claim 1 to mammalian skin, thereby effecting the administration of said medication.

9. The method according to claim 8, wherein said mammalian skin is human skin.

* * * * *